United States Patent [19]

Shanker et al.

[11] Patent Number: 5,488,060
[45] Date of Patent: Jan. 30, 1996

[54] SUBSTITUTED THIADIAZOLES, COMPOSITIONS CONTAINING THEM AND THEIR USE AS ANTIMICROBIAL AND MARINE ANTIFOULING AGENTS

[75] Inventors: Ravi B. Shanker; Duane R. Romer; R. Garth Pews, all of Midland, Mich.

[73] Assignee: The Dow Chemical Company, Midland, Mich.

[21] Appl. No.: 360,496

[22] Filed: Dec. 21, 1994

[51] Int. Cl.⁶ .................... A61K 31/41; A01N 43/832; C07D 285/10; C07D 417/04
[52] U.S. Cl. .................... 514/362; 514/342; 504/253; 504/261; 546/277; 548/135
[58] Field of Search .................... 514/342, 362; 546/277; 548/135

[56] References Cited

U.S. PATENT DOCUMENTS 3,753,999  8/1973  Tempel et al. .................... 260/306.6

Primary Examiner—Johann Richter
Assistant Examiner—Laura L. Stockton

Attorney, Agent, or Firm—S. Preston Jones; James M. Pelton

[57] ABSTRACT

Substituted thiadiazoles which correspond to the formula:

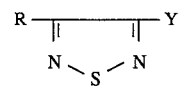

wherein R represents

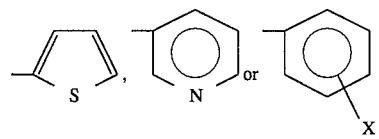

X represents —Br, —Cl, —F, —CH$_3$, —OCH$_3$, —COOCH$_3$, —NO$_2$, —SCH$_3$, —SO$_2$CH$_3$ or —CF$_3$ and Y is —SCN or —SCH$_2$SCN.

These compounds have been found to exhibit antimicrobial and marine antifouling activity in industrial and commercial applications and compositions containing these compounds are so employed.

24 Claims, No Drawings

SUBSTITUTED THIADIAZOLES, COMPOSITIONS CONTAINING THEM AND THEIR USE AS ANTIMICROBIAL AND MARINE ANTIFOULING AGENTS

FIELD OF THE INVENTION

The present invention is directed to novel substituted thiadiazole compounds, compositions containing said compounds and the use of these compositions as antimicrobial and marine antifouling agents.

SUMMARY OF THE INVENTION

The present invention is directed to compounds corresponding to the formula:

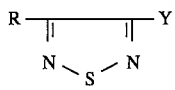

I wherein R represents

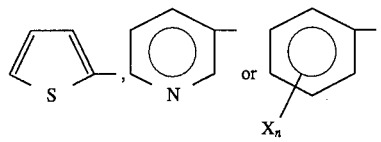

wherein X represents H, —Br, —Cl, —F, —CH$_3$, —OCH$_3$, —COOCH$_3$, —NO$_2$, —SCH$_3$, —SO$_2$CH$_3$ or —CF$_3$, n is an integer of from 0–5 and Y is —SCN or —SCH$_2$SCN.

The present invention is also directed to antimicrobial compositions comprising an inert diluent and an antimicrobially-effective amount of a compound corresponding to Formula 1.

The present invention is further directed to a method for inhibiting microorganisms in a microbial habitat comprising contacting said microbial habitat with an antimicrobially-effective amount of a compound corresponding to Formula 1.

The antimicrobial compositions of the present invention can also be employed to treat surfaces exposed to a marine environment in which marine organisms grow to prevent the growth of said marine organisms on said surfaces.

The preferred compounds of the present invention include those wherein R represents phenyl.

DETAILED DESCRIPTION OF THE INVENTION

In the present specification and claims the term "alkali metal" is employed to designate sodium, potassium, lithium or cesium.

In the present specification and claims, the term "halo" is employed to designate bromo, chloro, fluoro or iodo.

In the following process schematic formulas, certain specific alkali metals, halo groups, specific solvents and the like are set forth. These representations are only presented for convenience and are not to be considered as an indication that these specifically representations are the only groups or materials which can be employed.

In the present invention, it is to be noted that all substituent groups are sterically compatible with each other. The term "sterically compatible" is employed to designate substituent groups which are not affected by steric hindrance as this term is defined in "The Condensed Chemical Dictionary", 7th edition. Reinhold Publishing Co., N.Y. page 893 (1966) which definition is as follows:

"steric hindrance. A characteristic of molecular structure in which the molecules have a spatial arrangement of their atoms such that a given reaction with another molecule is prevented or retarded in rate."

Sterically compatible may be further defined as reacting compounds having substituents whose physical bulk does not require confinement within volumes insufficient for the exercise of their normal behavior as discussed in *Organic Chemistry* by D. J. Cram and G. Hammond, 2nd edition, McGraw-Hill Book Company, N.Y., page 215 (1964).

The substituted 1,2,5-thiadiazole compounds of the present invention can be prepared in a two-stage reaction procedure wherein in the first stage or step, a 4-substituted-3-halo-1,2,5-thiadiazole is reacted in the presence of a solvent such as dimethylformamide, N-methylpyrrolidone, or dimethylsulfoxide with an alkali metal sulfide, such as sodium sulfide to produce the corresponding 4-substituted-3-mercapto-1,2,5-thiadiazole: alkali metal salt, such as 4-substituted- 3-mercapto-1,2,5-thiadiazole: sodium salt.

The reactions are typically carried out at a temperature of from about 25° to about 40° C. The reactants may be added to the reaction mixture in any order of addition; conventionally they are added as a solution in the solvent used for the reaction. The reaction is conveniently allowed to continue over a period of from about 1 to about 24 hours. The reaction consumes the reactants in the ratio of one mole equivalent of the alkali metal sulfide per mole of the 4-substituted-3-halo-1,2,5-thiadiazole reactant. To assure the completion of the reaction, an excess of the alkali metal sulfide reactant is normally employed. The general scheme for this first reaction step is as follows:

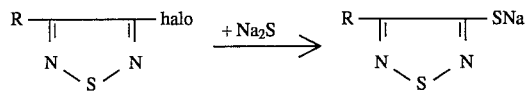

In carrying out the second reaction step, the above 4-substituted-3-mercapto-1,2,5-thiadiazole: alkali metal salt product is reacted in situ with a cyanogen halide, such as cyanogen bromide to prepare the desired 4-substituted-3-thiocyanato-1,2,5-thiadiazole product or with a halomethythiocyanate, such as chloromethylthiocyanate to prepare she desired 4-substituted-3-thiocyanatomethylthio-1,2,5-thiadiazole product. The reaction consumes the reactants in the ratio of one mole equivalent of the cyanogen halide or halomethylthiocyanate per mole of the 4-substituted-3-mercapto- 1,2,5-thiadiazole: alkali metal salt reactant. To assure the completion of the reaction, a slight excess of the cyanogen halide or halomethylthiocyanate reactant is normally employed. The general reaction schemes (A and B) for this second step is as follows:

Reaction Scheme A

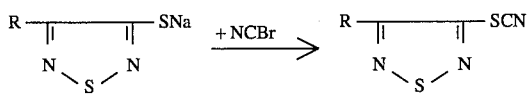

Reaction Scheme B

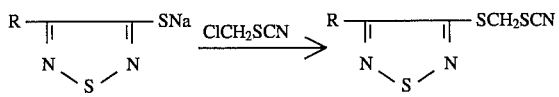

In the above formulae R is as hereinabove defined.

The above second stage reactions are typically carried out at a temperature of from about 25 to about 40° C. The reactants may be added to the reaction mixture in any order of addition; conventionally they are added as a solution in the solvent used for the reaction. Subsequent to the addition of the reactants, the reaction is allowed to continue over a period of about 1 to about 24 hours. The reaction product may be isolated by adding a 3 to 10 volume excess of water which will precipitate the desired product. Filtration followed by washing and drying yields the desired compounds of the present invention.

Preparation of Starting Materials

Chloromethylthiocyanate is well known and is described in JP-B-62215561 and JP-B-62215562.

The 4-substituted-3-halo-1,2,5-thiadiazole reactant corresponding to the formula

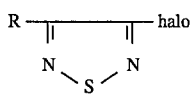

wherein R is as hereinabove defined are known compounds. The compounds are well known in the literature. The compounds wherein R is phenyl or substituted phenyl are either specifically taught or they can be prepared as described by L. M. Weinstock et al. in the Journal of Organic Chemistry, Vol. 32, pages 2823–29, (1967); or in U.S. Pat. No. 4,555,521. Other references include Japanese Patents JPO 5,163,257 A2; 5,163,258 A2; and 5,163,259 A2.

The 4,5-Dichloro-1,2,5-thiadiazole reactant is described in U.S. Pat. No. 3,115,497.

The synthesis of cyanogen bromide is described in Organic Synthesis Collective, Vol. 2, page 150, (1943):

The following examples illustrate the present invention and the manner by which it can be practiced but, as such, should not be construed as limitations upon the overall scope of the same.

Since the hereinabove and hereinafter set forth compound preparation procedures employ only standard chemistry practices and it is known that slightly different reactants can require slightly different reaction parameters from those for other reactants, it is to be understood that minor modifications to the reaction parameters set forth such as the use of an excess of one reactant, the use of a catalyst, the use of high temperature and/or high pressure equipment, high speed mixing and other such conventional changes are within the scope of the present invention.

The desired product can be separated from the reaction product of the above preparative procedures employing conventional separatory procedures known to those skilled in the art including steps of solvent extraction, filtration, water washing, column chromatography, neutralization, acidification, crystallization and distillation.

The structure identity of all compounds is confirmed by proton nuclear magnetic resonance spectroscopy ($^1$H NMR), recorded at 300 MHz; carbon nuclear magnetic resonance spectroscopy ($^{13}$C NMR) recorded at 75 MHz; infrared spectroscopy (IR) and gas chromatography/mass spectrometry (GC/MS). All of the reactions are conducted under a positive pressure of nitrogen.

Example I: Preparation of 4-Phenyl-3-thiocyanato-1,2,5-thiadiazole

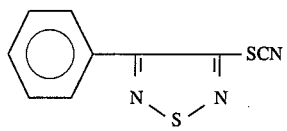

To a stirred solution of 3.8 grams(g)(0.05 mole) of sodium sulfide in 100 mL of dimethylformamide was added 8 g(0.041 mole) of 4-Phenyl-3-chloro- 1,2,5-thiadiazole. The mixture was stirred overnight (~16 hours), and to the resulting dark green solution was added 6.64 g(1.5 molar equivalents) of cyanogen bromide. This mixture was stirred for about 14 hours and then diluted with 100 mL of water and extracted with 200 mL of methylene chloride. The organic layer was separated and washed with water (2×100 mL), dried and concentrated under reduced pressure. The thus recovered crude material was chromatographed on silica gel with a 10% EtoAc:90% hexane mixture to yield 6.6 g (72 percent of theoretical) as an oil which turned to a white solid melting at 49° C. upon standing; $^{13}$C NMR (75 MHz, CDCl$_3$) δ 159.10, 141.78, 130.59, 129.76, 129.06, 127.88, 105.98; MS (EI) m/e 219(M$^+$), 192, 160, 135, 103.

By employing the above preparative procedure employing the appropriate starting materials, the following compounds were prepared.

Example II: Preparation of 4-(4-Chlorophenyl)-3-thiocyanato-1,2,5-thiadiazole

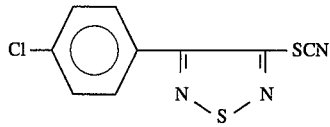

This compound was isolated as a white solid which melted at 87°–88° C. in a yield of 65 percent of theoretical; $^1$H NMR (300 MHz, CDCl$_3$) δ 7.67 (d, J=8.3 Hz, 2H), 7.53 (dr J=8.3 Hz, 2H): $^{13}$C NMR (75 MHz, CDCl$_3$) δ 158.21, 141.66, 137.04, 129.45, 129.31,128.29, 105.733; MS (EI) m/e 255, 253, 194, 171, 169, 139, 137, 116, 102.

Example III: Preparation of 4-(3-Chlorophenyl)-3-thiocyanato-1,2,5-thiadiazole

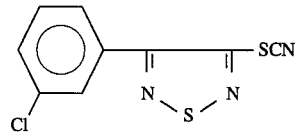

This compound was isolated as a white solid which melted at 82°–83° C. in a yield of 53 percent of theoretical; $^1$H NMR (300 MHz, CDCl$_3$) δ 7.72 (s, 1H), 7.08 (d, J=6.9 Hz. 1H), 7.54 (m, 1H), 7.48 (m, 1H); $^{13}$C NMR (75 MHz, CDCl$_3$) δ 157.76, 141.83, 135.22, 131.40, 130.73, 130.34, 128.24, 125.87, 105.59; MS (EI) m/e 255, 253, 228, 226, 218, 196, 194, 171, 169, 139, 137, 102.

Example IV: Preparation of 4-(2-Chlorophenyl)-3-thiocyanatol-1,2,5-thiadiazole

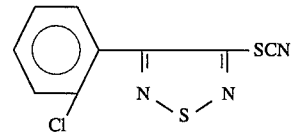

This compound was isolated as an oil in a yield of 55 percent of theoretical; $^{13}$C NMR (75 MHz, CDCl$_3$) δ 158.12, 143.88, 131.92, 131.22, 131.22, 130.03, 129.90, 127.75, 106.33; MS (EI) m/e 255, 253, 218, 171, 169, 139, 137, 116, 102.

Example V: Preparation of 4-(4-Fluorophenyl)-3-thiocyanato-1,2,5-thiadiazole

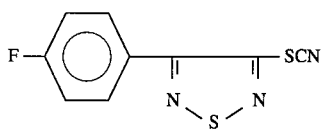

This compound was isolated as a white solid which melted at 67°–68° C. in a yield of 60 percent of theoretical; $^1$H NMR (300 MHz, CDCl$_3$) δ 7.70–7.74 (dd, J=8.3, 5.2 Hz, 2H), 7.24 (t, J=8.5 Hz, 2H); $^{13}$C NMR (75 MHz, CDCl$_3$) δ 165.46, 162.12, 158.31, 142.00, 130.21, 130.10, 126.05, 116.54, 116.25, 105.80; MS (EI) m/e 237(M$^+$), 210, 178, 153, 121, 116.

Example VI: Preparation of 4-(4-Bromophenyl)-3-thiocyanato-1,2,5-thiadiazole

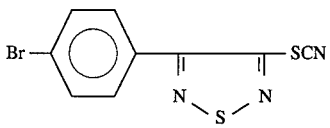

This compound was isolated as a yellow solid which melted at 105° C. in a yield of 70 percent of theoretical; $^1$H NMR (300 MHz, CDCl$_3$) δ 7.68 (d, J=8.5 Hz, 2H), 7.59 (d, J=8.5 Hz, 2H); $^{13}$C NMR (75 MHz, CDCl$_3$) δ 158.20, 141.60, 132.35, 129.43, 128.69, 125.36, 105.69; MS (EI) m/e 299, 297, 272, 270, 218, 215, 213, 183, 181, 160, 116.

Example VII: Preparation of a-(3-Methoxyphenyl)-3-thiocyanato-1,2,5-thiadiazole

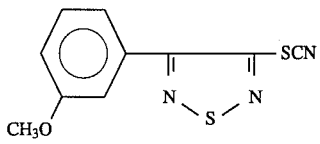

This compound was isolated as a yellow solid which melted at 64°–65° C. in a yield of 50 percent of theoretical; 1H NMR (300 MHz, CDCl$_3$) δ 7.45 (d, J=8.3 Hz, 2H), 7.22 (s, 1H), 7.07 (dd, J=8.3, 2.2 Hz, 1H), 3.88 (s, 3H); $^{13}$C NMR (75 MHz, CDCl$_3$) δ 159.83, 158.85, 141.98, 130.18, 119.90, 116.53, 113.42, 105.96, 55.47; MS (EI) m/e 249(M$^+$), 222, 190, 175, 159, 147.

Example VIII: Preparation of 4-(4-Methoxyphenyl)-3-thiocyanato-1,2,5-thiadiazole

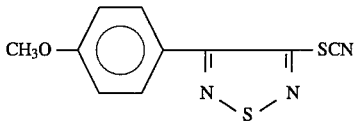

This compound was isolated as a white solid which melted at 121° C. in a yield of 60 percent of theoretical; $^1$H NMR (300 MHz, CDCl$_3$) δ 7.64 (d, J=8.7 Hz, 2H), 7.32 (d, J=8.6 Hz, 2H), 3.88 (s, 3H); $^{13}$C NMR (75 MHz, CDCl$_3$) δ 161.22, 158.93. 141.50, 129.46, 122.27, 111.50, 106.43, 55.45; MS (EI) m/e 249(M$^+$), 226, 165, 133, 103, 90.

Example IX: Preparation of 4-(4-Methylthiophenyl)-3-thiocyanato-1,2,5-thiadiazole

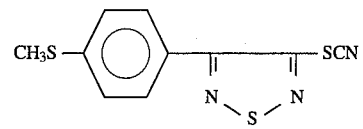

This compound was isolated as a yellow solid which melted at 80°–82° C. in a yield of 46 percent of theoretical; $^1$H NMR (300 MHz, CDCl$_3$) δ 7.62 (d, J=8.7 Hz, 2H), 7.35 (d, J=8.7 Hz, 2H), 2.53 (s, 3H); $^{13}$C NMR (75 MHz, CDCl$_3$) δ 158.86, 142.76, 141.63, 128.62, 128.13, 125.88, 125.56, 105.98, 15.13; MS (EI) m/e 265(M$^+$), 205, 192, 181, 149, 116.

Example X: Preparation of 4-(4-Trifluoromethylphenyl)-3-thiocyanato-1,2,5-thiadiazole

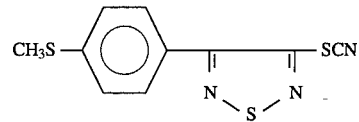

This compound was isolated as a white solid which melted at 76° C. in a yield of 65 percent of theoretical; $^1$H NMR (300 MHz, CDCl$_3$) δ 7.87 (d, J=8.4 Hz, 2H), 7.81 (d, J=8.4 Hz, 2H); $^{13}$C NMR (75 MHz, CDCl$_3$) δ 158.94, 142.06, 133.33, 132.85, 132.42, 128.65, 128.38, 126.26, 121.72, 105.69; MS (EI) m/e 287(M$^+$), 260, 203, 116.

Example XI: Preparation of 4-(4-Methylsulfonylphenyl)-3-thiocyanato-1,2,5-thiadiazole

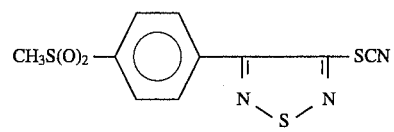

This compound was isolated as a tan solid which melted at 158°–160° C. in a yield of 66 percent of theoretical; $^1$H NMR (300 MHz, CDCl$_3$) δ 8.13 (d, J=8.1 Hz, 2H), 7.96 (d, J=8.2 Hz, 2H), 3.13 (s, 3H); $^{13}$C NMR (75 MHz, CDCl$_3$) δ 157.43, 142.24, 134.80, 129.35, 129.05, 128.18, 105.39, 44.45.

Example XII: Preparation of 4-(4-Carboxymethylphenyl)-3-thiocyanato-1,2,5-thiadiazole

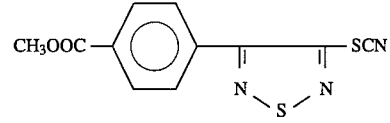

This compound was isolated as a yellow solid which melted at 135° C. in a yield of 48 percent of theoretical; $^1$H NMR (300 MHz, CDCl$_3$) δ 8.21 (d, J=8.2 Hz, 2H), 7.81 (d, J=8.2 Hz, 2H), 3.97 (s,3H); $^{13}$C NMR (75 MHz, CDCl$_3$) δ 165.64, 158.17, 141.97, 133.73, 131.90, 130.19, 127.99, 105.58, 52.54; MS (EI) m/e 278(M$^+$), 246, 130, 102.

Example XIII: Preparation of 4-(4-nitrophenyl)-3-thiocyanato-1,2,5-thiadiazole

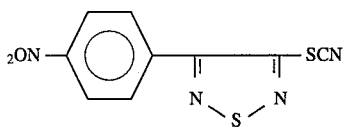

This compound was isolated as a yellow solid which melted at 117° C. in a yield of 48 percent of theoretical; $^1$H NMR (300 MHz, CDCl$_3$) δ 8.42 (d, J=8.8 Hz, 2H), 7.97 (d, J=8.8 Hz, 2H); $^{13}$C NMR (75 MHz, CDCl$_3$) 157.06, 148.56, 141.93, 135.47, 129.10, 124.19, 105.27; MS (EI) m/e 264(M$^+$), 218.

Example XIV: Preparation of 4-(2-Thiophene)-3-thiocyanato-1,2,5-thiadiazole

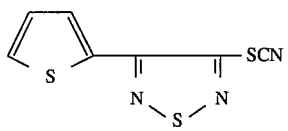

This compound was isolated as a white solid which melted at 70°–71° C. in a yield of 48 percent of theoretical; $^1$H NMR (300 MHz, CDCl$_3$) δ 7.62 (d, J=3.5 Hz, 1H), 7.57 (d, J=5 Hz, 1H), 7.19 (dd, J=3.5, 5.0 Hz, 1H); $^{13}$C NMR (75 MHz, CDCl$_3$) δ 153.33, 140.01, 132.10, 130.04, 128.20, 128.12, 105.63; MS (EI) m/e 225(M$^+$), 198, 180, 141, 116.

Example XV: Preparation of 4-(3-Pyridyl)-3-thiocyanato-1,2,5-thiadiazole

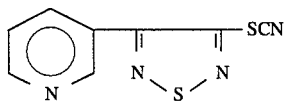

This compound was isolated as a yellow solid which melted at 120° C. in a yield of 45 percent of theoretical; $^1$H NMR (300 MHz, CDCl$_3$) δ 8.97 (s, 1H), 7.58 (d, J=3.8 Hz, 1H), 8.06 (d, J=7.8 Hz, 1H), 7.48 (m, 1H); $^{13}$C NMR (75 MHz, CDCl$_3$) δ 156.74, 151.34, 148.48, 141.77, 135.33, 126.16, 123.64, 105.48; MS (EI) m/e 220(M$^+$), 194, 156, 136, 130, 116.

Example XVI: Preparation of 4-Phenyl-3-thiocyanato-methylthio-1,2,5-thiadiazole

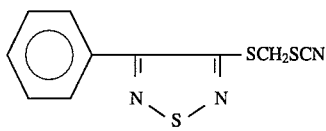

To a stirred solution of 3.81 grams(g)(0.05 mole) of sodium sulfide in 100 mL of dimethylformamide was added 8 g (0.041 mole) of 4-Phenyl-3-chloro- 1,2,5-thiadiazole. The mixture was stirred 18 hours and to this mixture was added 6.68 g (1.5 molar equivalents) of chloromethyithio- cyanate. This mixture was stirred for ~14 hours and then diluted with 100 mL of water and extracted with 200 mL of methylene chloride. The organic layer was separated and washed with water (2×100 mL), dried and concentrated under reduced pressure. The thus recovered crude material was chromatographed on silica gel with a 10% EtoAc:90% hexane mixture to yield 8.99 g (83 percent of theoretical) as an oil. Upon crystallization, a light yellow solid melting at 58°–60° C. was recovered in a yield of 69 percent of theoretical; $^1$H NMR (300 MHz, CDCl$_3$)δ 4.77 (s, 2H), 7.49 (m, 3H), 7.82 (m, 2H); $^{13}$C NMR (75 MHz, CDCl$_3$) δ 38.28, 111.46, 127.97, 128.78, 130.06, 151.77, 157.93; MS (EI) m/e 265(M$^+$), 207, 148, 116.

By employing the above preparative procedure employing the appropriate starting materials, the following compounds were prepared.

Example XVII: Preparation of 4-(4-Bromophenyl)-3-thiocyanatomethylthio-1,2,5-thiadiazole

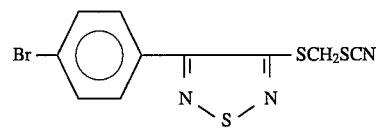

This compound was isolated as a tan solid which melted at 67°–68° C. in a yield of 65 percent of theoretical; $^1$H NMR (300 MHz, CDCl$_3$) δ 4.79 (s, 2H), 7.63 (dr J=8.4 Hz, 2H), 7.30 (d, J=8.4 Hz, 2H); $^{13}$C NMR (75 MHz, CDCl$_3$) δ 38.31, 111.32, 129.48, 129.78, 132.01, 151.62, 156.75; MS (EI) m/e 345, 343, 287, 285, 206.

Example XVIII: Preparation of 4-(4-Chlorophenyl)-3-thiocyanatomethylthio- 1,2,5-thiadiazole

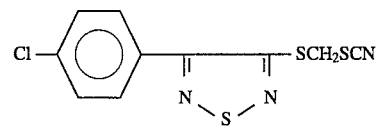

This compound was isolated as a white solid which melted at 62°–63° C. in a yield of 60 percent of theoretical; $^1$H NMR (300 MHz, CDCl$_3$) δ 4.80 (s, 2H), 7.48 (dr J=8.2 Hz, 2H), 7.79 (dr J=8.2 Hz7 2H); $^{13}$C NMR (75 MHz, CDCl$_3$) δ 38.33, 111.327 129.097 129.32, 136.28, 151.667 156.75; MS (EI) m/e 301(M$^+$+1), 299, 243, 241, 182, 150.

Example XIX: Preparation of 4-(3-Chlorophenyl)-3-thiocyanatomethylthio-1,2,5-thiadiazole

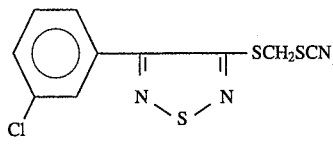

This compound was isolated as a white solid which melted at 67° C. in a yield of 52 percent of theoretical; $^1$H NMR (300 MHz, CDCl$_3$) δ 2.80 (s, 2H), 7.72 (mr 1H), 7.83 (s, 1H) $^{13}$C NMR (75 MHz, CDCl$_3$) δ 38.30, 111.23, 125.90, 128.18, 129.99, 130.09, 132.44, 134.83, 151.75, 156.35; MS (EI) m/e 301(M$^+$+1), 299, 243, 241, 202, 182.

Example XX: Preparation of 4-(2-Chlorophenyl)-3-thiocyanatomethylthio-1,2,5-thiadiazole

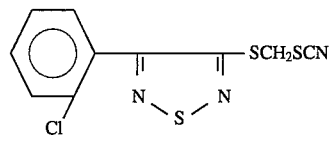

This compound was isolated as an oil in a yield of 52 percent of theoretical; $^1$H NMR (300 MHz, CDCl$_3$) δ 4.74 (s, 2H), 7.41–7.52 (m, 4H); $^{13}$C NMR (75 MHz, CDCl$_3$) δ 38.08, 111.15, 126.90, 129.81, 130.15, 130.86, 131.32, 133.32, 153.64, 156.34; MS (EI) m/e 301(M$^+$+1), 299, 205, 184, 182, 150.

Example XXI: Preparation of 4-(4-Fluorophenyl)-3-thiocyanatomethylthio- 1,2,5-thiadiazole

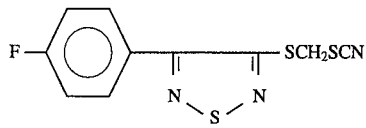

This compound was isolated as a clear oil in a yield of 65 percent of theoretical; $^1$H NMR (300 MHz, CDCl$_3$) δ 4.80 (s, 2H), 7.20 (t, J=8.5 Hz, 2H), 7.84 (m, 2H) $^{13}$C NMR (75 MHz, CDCl$_3$) δ 38.32, 11.36, 115.85, 116.44, 127.15, 130.04, 130.16, 151.51, 156.51, 161.79, 165.12.

Example XXII: Preparation of 4-(3-Methoxyphenyl)-3-thiocyanatomethylthio-1,2,5-thiadiazole

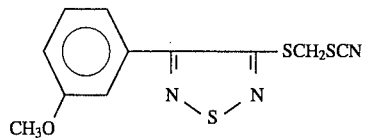

This compound was isolated as a yellow oil with a yield of 70 percent of theoretical; $^1$H NMR (300 MHz, CDCl$_3$) δ 3.87 (s, 3H), 4.79 (s, 2H). 7.05 (m, 1H), 7.42 (m, 3H); $^{13}$C NMR (75 MHz, CDCl$_3$) δ 38.36, 55.47, 111.39, 113.23, 116.20, 120.17, 129.84, 132.03, 151.81, 157.73, 159.60; MS (EI) m/e 295(M$^+$), 237, 178, 146.

Example XXIII: Preparation of 4-(4-Methoxyphenyl)- 3-thiocyanatomethylthio-1,2,5-thiadiazole

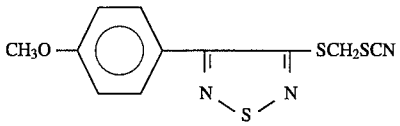

This compound was isolated as a white solid which melted at 79°–80° C. in a yield of 69 percent of theoretical; 1H NMR (300 MHz CDCl$_3$) δ 3.87 (s, 3H), 4.78 (s, 2H), 7.02 (d. J=8.52 Hz, 2H). 7.79 (d, J=8.52 Hz, 2H); $^{13}$C NMR (75 MHz, CDCl$_3$) δ 38.41, 55.41, 11.52, 114.17, 123.54, 129.18, 151.23, 157.68, 160.79: MS (EI) m/e 295, 237, 178, 146.

Example XXIV: Preparation of 4-(4-Methylthiophenyl)-3-thiocyanatomethylthio-1,2,5-thiadiazole

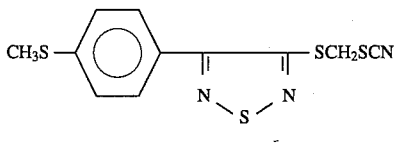

This compound was isolated as a white solid which melted at 79°–80° C. in a yield of 64 percent of theoretical; $^1$H NMR (300 MHz, CDCl$_3$) δ 2.53 (s, 3H), 4.78 (s, 2H), 7.34 (d, J=8.71 Hz, 2H), 7.76 (d, J=8.1 Hz, 2H); $^{13}$C NMR (75 MHz, CDCl$_3$) δ 15.26, 38.38, 111.36, 25.73, 127.22, 128.17, 141.72, 151.44, 157.36; MS (EI) m/e 311(M$^+$), 253, 206.

Example XXV: Preparation of 4-(4-Methylsulfonylphenyl)-3-thiocyanatomethylthio-1,2,5-thiadiazole

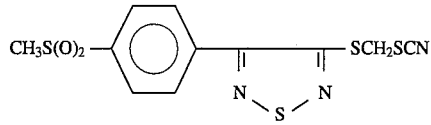

This compound was isolated as a white solid which melted at 120°–121° C. in a yield of 54 percent of theoretical; $^1$H NMR (300 MHz, CDCl$_3$) δ 3.13 (s, 3H), 4.84 (s, 2H), 8.09 (q, 4H); $^{13}$C NMR (75 MHz, CDCl$_3$) δ 38.21, 44.48, 111.12, 127.86, 128.95, 135.81, 141.48, 152.08, 155.80.

Example XXVI: Preparation of 4-(4-Trifluoromethyl-phenyl)-3-thiocyanatomethylthio- 1,2,5-thiadiazole

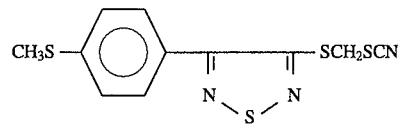

This compound was isolated as a white solid which melted at 79°–80° C. in a yield of 74 percent of theoretical; $^1$H NMR (300 MHz, CDCl$_3$) δ 4.81 (s, 2H), 7.78 (d, J=8.2 Hz, 2H), 7,98 (d, J=8.2 Hz, 2H); $^{13}$C NMR (75 MHz, CDCl$_3$) δ 138.26, 111.19, 121.73, 125.33, 125.78, 125.82, 128.43, 131,61, 132.04, 134.18, 151.96, 156,42; MS (EI) m/e 333(M$^+$), 275, 216, 184.

Example XXVII: Preparation of 4-(4-Methylphenyl)- 3-thiocyanatomethylthio-1,2,5-thiadiazole

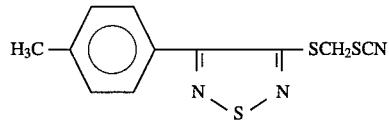

This compound was isolated as a yellow oil in a yield of 42 percent of theoretical: $^1$H NMR (300 MHz, CDCl$_3$) δ 2.42 (s, 3H), 4.76 (s, 2H), 7.29 (d, J=7.7 Hz, 1H), 7.38 (t, J=7.6 Hz, 1H), 7.60 (m, 2H); $^{13}$C NMR (75 MHz, CDCl$_3$) δ 21.40, 38.26, 111.49, 125.03, 128.70 130.92, 138.73, 151.92, 158.25.

Example XXVIII: Preparation of 4-(4-Carboxymethyl-phenyl)-3-thiocyanatomethylthio- 1,2,5-thiadiazole

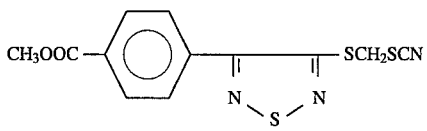

This compound was isolated as a white solid which melted at 119°–120° C. in a yield of 65 percent of theoretical; $^1$H NMR (300 MHz, CDCl$_3$) δ 3.96 (s, 3H), 4.81 (s, 2H), 7.93 (d, J=8.3 Hz, 2H), 8.17 (d, J=8.3 Hz, 2H); $^{13}$C NMR (75 MHz, CDCl$_3$) δ 38.31, 52.44, 111.21, 127.97, 129.93, 131.28, 134.82, 152.01, 156.767 165.90; MS (EI) m/e 323(M$^+$), 265, 221, 205, 162, 130.

Example XXIX: Preparation of 4-(4-Nitrophenyl)-3-thiocyanatomethylthio-1,2,5-thiadiazole

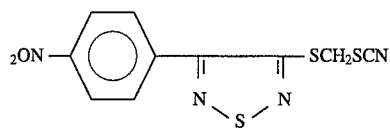

This compound was isolated as a yellow solid which melted at 78° C. in a yield of 56 percent of theoretical: $^1$H NMR (300 MHz. CDCl$_3$) δ 4.86 (s, 2H), 8.06 (d, J=8.8 Hz, 2H), 8.36 (d, J=8.8 Hz, 2H); $^{13}$C NMR (75 MHz, CDCl$_3$) δ 38.32, 111.13, 123.98, 129.02, 136.60, 148.19, 152.22, 155.43; MS (EI) m/e 310(M$^+$), 252, 206.

Example XXX: Preparation of 4-(2-Thiophene)-3-thiocyanatomethylthio-1,2,5-thiadiazole

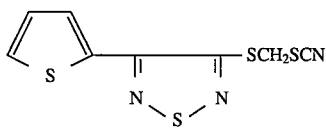

This compound was isolated as a tan solid which melted at 120°–122° C. in a yield of 67 percent of theoretical; $^1$H NMR (300 MHz, CDCl$_3$) δ 7.16 (dd, J=4.8, 3.6 Hz, 1H), 7.71 (d, J=3.6 Hz, 1H); $^{13}$C NMR (75 MHz, CDCl$_3$) δ 38.23, 111.30, 127.56, 126.63, 129.14, 133.53, 150.44, 151.93; MS (EI) m/e 271(M$^+$), 213, 180, 154, 122.

Example XXXI: Preparation of 4-(3-Pyridyl)-3-thiocyanatomethylthio-1,2,5-thiadiazole

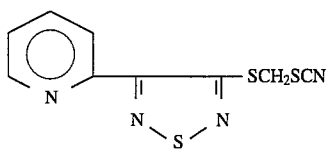

This compound was isolated as a yellow solid which melted at 88°–90° C. in a yield of 77 percent of theoretical; $^1$H NMR (300 MHz, CDCl$_3$) δ 4.84 (s, 2H), 7.46 (dd, J=4.7, 7.9 Hz, 1B), 8.17 (d, J=7.9 Hz, 1H), 8.73 (d, J=7.9Hz, 1H), 9.10 (s, 1H); $^{13}$C NMR (75 MHz, CDCl$_3$) δ 38.24, 111.08, 123.39, 127.11, 135.11, 148.75, 150.73, 151.93, 155.08; MS (EI) m/e 266(M$^+$), 208, 149, 118.

Antimicrobial Activity

The compounds of this invention are useful as antimicrobial additives, and they can be added to industrial products such as paints, inks, adhesives, soaps, cutting oils, textiles, paper pigment slurries and styrene-butadiene latexes used for paper coatings to provide needed antimicrobial properties.

The compounds are also used as antimicrobial additives in such personal care products as hand creams, lotions, shampoos and hand soaps. A further advantage in the use of the compounds of this invention is their cost-effectiveness for applications which need to have an antimicrobial continuously replenished, such as in cooling towers and pulp and paper mills.

As appreciated by those skilled in the art, each of the compounds disclosed herein are not necessarily active at the same concentrations or against the same microbial species. There may be some compound-to-compound variation in antimicrobial potency and spectrum of antimicrobial activity.

The antimicrobial compounds of the present invention may be added to formulations susceptible to microbial growth. They may be added either undiluted or dissolved in inert diluents such as organic solvents such as glycols, alcohols or acetone. They may also be added alone or in combination with other preservatives.

As used herein, the term "microorganism" is meant to refer to bacteria, fungi, viruses, algae, subviral agents and protozoa.

As used herein, the term "antimicrobially-effective amount" refers to that amount of one or a mixture of the compounds, or of a composition comprising such compound or compounds, of this invention needed to exhibit inhibition of selected microorganisms. Typically, this amount varies from providing about 1 part per million (ppm) to about 5,000 ppm by weight of the compound to a microbial habitat being contacted with the compound. Such amounts typically vary depending upon the particular compound tested and microorganism treated. Additionally, the exact concentration of the compounds to be added in the treatment of industrial and consumer formulations may vary within a product type depending upon the components of the formulation. A preferred effective amount of the compound is from about 1 ppm to about 500 ppm, more preferably from about 1 ppm to about 50 ppm by weight, of a microbial habitat.

The term "habitat" refers to a place or site where a microorganism naturally or normally lives or grows. Typically, such a habitat will be an area that provides a moisture source, nutrient source, and/or an oxygen source such as, for example, a cooling water tower or an air washing system.

The terms "inhibition", "inhibit" or "inhibiting" refer to the suppression, stasis, kill, or any other interference with the normal life processes of microorganisms that is adverse to such microorganisms, so as to destroy or irreversibly inactivate existing microorganisms and/or prevent or control their future growth and reproduction.

The antimicrobial activity of the compounds of the present invention is set forth as the minimum inhibitory concentration (MIC) for the active compounds and is determined for nine (9) bacteria, using nutrient agar, and seven (7) yeast and fungi, using malt yeast agar. This determination is conducted using a one percent solution of the test compound prepared in a mixture of acetone and water.

Nutrient agar is prepared at pH 6.8, representing a neutral medium, and at pH 8.2, representing an alkaline medium. The nutrient agars are prepared by adding 23 g of nutrient agar to one-liter of deionized water. In addition, the alkaline medium is prepared by adjusting a 0.04M solution of N-[tris-(hydroxymethyl)methyl]glycine buffered deionized water with concentrated sodium hydroxide to a pH of 8.5.

Malt yeast agar is prepared at pH 5.5 by adding 3 g yeast extract and 45 g malt agar per liter of deionized water. The specific agar is dispensed in 30 mL aliquots into 25×200 mm test tubes, capped and autoclaved for 15 minutes at 115° C.

The test tubes containing the agar are cooled in a water bath until the temperature of the agar is 48° C. Then, an appropriate amount of the one percent solution of the test compound is added (except in the controls where no compound is added) to the respective test tubes so that the final concentrations are 500, 50, 100, 50, 25, 10, 5, 2.5, 1.0 and zero parts per million of the test compound in the agar, thus having a known concentration of test compound dispersed therein. The contents of the test tubes are then transferred to respective petri plates. After drying for 24 hours, the petri plates containing nutrient agar are inoculated with bacteria and those containing malt yeast agar are inoculated with yeast and fungi.

The inoculation with bacteria is accomplished by using the following procedure. Twenty-four hour-cultures of each of the bacteria are prepared by incubating the respective bacteria in tubes containing nutrient broth for 24 hours at 30° C. in a shaker. Dilutions of each of the 24 hour-cultures are made so that nine separate suspensions (one for each of the nine test bacteria) are made, each containing $10^8$ colony forming units (CFU) per mL of suspension of a particular bacteria. Aliquots of 0.3 mL of each of the bacterial suspensions are used to fill the individual wells of Steer's Replicator. For each microbial suspension, 0.3 mL was used to fill three wells (i.e., three wells of 0.3 mL each) so that for the nine different bacteria, 27 wells are filled. The Steer's Replicator is then used to inoculate both the neutral and alkaline pH nutrient agar petri plates.

The inoculated petri plates are incubated at 30° C. for 48 hours and then read to determine if the test compound which is incorporated into the agar prevented growth of the respective bacteria.

The inoculation with the yeast and fungi is accomplished as follows. Cultures of yeast and fungi are incubated for seven days on malt yeast agar at 30° C. These cultures are used to prepare suspensions by the following procedure. A suspension of each organism is prepared by adding 10 mL of sterile saline and 10 microliters of octylphenoxy polyethoxy ethanol to the agar slant of yeast or fungi. The sterile saline/octylphenoxy potyethoxy ethanol solution is then agitated with a sterile swab to suspend the microorganism grown on the slant. Each resulting suspension is diluted into sterile saline (1 part suspension: 9 parts sterile saline). Aliquots of these dilutions are placed in individual wells of Steer's Replicator and petri plates inoculated as previously described. The petri plates are incubated at 30° C. and read after 48 hours for yeast and 72 hours for fungi.

Table I lists the bacteria, yeast and fungi used in the MIC test described above along with their respective American Type Culture Collection (ATCC) identification numbers.

TABLE I

Organisms Used in the Minimum Inhibitory Concentration Test

| Organism | ATCC No. |
|---|---|
| Bacteria | |
| Bacillus subtilis (Bs) | 8473 |
| Enterobacter aerogenes (Ea) | 13048 |
| Escherichia coli (Ec) | 11229 |
| Klebsiella pneumoniae (Kp) | 8308 |
| Proteus vulgaris (Pv) | 881 |
| Pseudomonas aeruginosa (Pa) | 10145 |
| Pseudomonas aeruginosa (PRD-10) | 15442 |
| Salmonella choleraesuis (Se) | 10708 |
| Staphylococcus aureus (Sa) | 6538 |
| Yeast/Fungi | |
| Aspergillus niger (An) | 16404 |
| Candida albicans (Ca) | 10231 |
| Penicillium chrysogenum (Pc) | 9480 |
| Saccharomyces cerevisiae (Sc) | 4105 |
| Trichoderma viride (Tv) | 8678 |
| Aureobasidium pullulan (Ap) | 16622 |
| Fusarium oxysporum (Fo) | 48112 |

In Tables II and III, the MIC values of the active compounds of the present invention as compared to the MIC of a standard commercial preservative (with 1-(3-chloroallyl)-3,5,7-triaza-1-azoniaadamantane chloride as the active agent and referred to in Tables II and III as "STANDARD I") are set forth for the bacteria organisms and yeast/fungi organisms which are listed in Table I.

TABLE II

Minimum Inhibitory Concentrations for Test Compounds in Bacteria Species (in ppm)

| Compound (Example No.) | | Bs | Ea | Ec | Kp | Pv | PRD | Pa | SC | Sa |
|---|---|---|---|---|---|---|---|---|---|---|
| STANDARD I | pH 6.8 | 50 | 100 | 100 | 50 | 50 | 100 | 100 | 50 | 100 |
|  | pH 8.2 | 250 | 250 | 250 | 250 | 250 | 500 | >500 | 100 | 250 |
| (I) | pH 6.8 | <10 | 100 | 50 | 25 | 50 | >500 | >500 | 50 | 25 |
|  | pH 8.2 | 250 | 500 | >500 | 500 | 500 | >500 | >500 | >500 | 500 |
| (II) | pH 6.8 | 250 | >500 | 50 | 50 | >500 | >500 | >500 | >500 | 250 |
|  | pH 8.2 | 500 | >500 | >500 | 250 | >500 | >500 | 500 | 500 | 500 |
| (III) | pH 6.8 | 25 | >500 | 50 | 50 | >500 | >500 | >500 | 50 | 25 |
|  | pH 8.2 | 100 | >500 | 500 | 500 | 500 | 500 | 500 | 500 | 250 |
| (IV) | pH 6.8 | <10 | >500 | 250 | >500 | >500 | >500 | >500 | 100 | 25 |
|  | pH 8.2 | 250 | 500 | 500 | 500 | 500 | 500 | 500 | 500 | 500 |
| (V) | pH 6.8 | <10 | 250 | 50 | 100 | 25 | 250 | 100 | 100 | 25 |
|  | pH 8.2 | 50 | 500 | 250 | 100 | 100 | 250 | 100 | 250 | 50 |
| (VI) | pH 6.8 | 25 | 500 | 500 | 500 | 500 | 500 | 500 | 500 | 50 |
|  | pH 8.2 | 500 | 500 | 500 | 500 | 500 | 500 | 500 | 500 | 500 |

TABLE II-continued

Minimum Inhibitory Concentrations for Test Compounds in Bacteria Species (in ppm)

| Compound (Example No.) | | Bs | Ea | Ec | Kp | Pv | PRD | Pa | SC | Sa |
|---|---|---|---|---|---|---|---|---|---|---|
| (VII) | pH 6.8 | 25 | >500 | >500 | >500 | >500 | >500 | >500 | >500 | 250 |
| | pH 8.2 | 250 | 500 | 500 | 500 | 500 | 500 | 500 | 500 | 500 |
| (VIII) | pH 6.8 | 100 | >500 | >500 | >500 | >500 | >500 | >500 | >500 | >500 |
| | pH 8.2 | >500 | >500 | >500 | >500 | >500 | >500 | >500 | >500 | >500 |
| (IX) | pH 6.8 | <10 | >500 | >500 | >500 | >500 | >500 | >500 | >500 | 50 |
| | pH 8.2 | 250 | 500 | 500 | 500 | 500 | 500 | 500 | 500 | 250 |
| (X) | pH 6.8 | 25 | >500 | >500 | >500 | >500 | >500 | >50 | >500 | >500 |
| | pH 8.2 | 500 | 500 | 500 | 500 | 500 | 500 | 500 | 500 | 500 |
| (XI) | pH 6.8 | 25 | 500 | 500 | 250 | 500 | 500 | 500 | 500 | 100 |
| | pH 8.2 | 5001 | 500 | 500 | 500 | 500 | 500 | 500 | 500 | 500 |
| (XII) | pH 6.8 | 25 | 500 | 500 | 500 | 500 | 500 | 500 | 500 | 500 |
| | pH 8.2 | 500 | 500 | 500 | 500 | 500 | 500 | 500 | 500 | 500 |
| (XIII) | pH 6.8 | 25 | 500 | 500 | 100 | 500 | 500 | 500 | 500 | 50 |
| | pH 8.2 | >100 | >100 | >100 | >100 | >100 | >100 | >100 | >100 | >100 |
| (XIV) | pH 6.8 | 25 | 100 | 50 | 25 | 50 | 500 | 500 | 50 | 25 |
| | pH 8.2 | 100 | 500 | 500 | 500 | 500 | 500 | 500 | 500 | 500 |
| (XV) | pH 6.8 | 25 | 250 | 250 | 100 | 100 | 500 | 500 | 250 | 50 |
| | pH 8.2 | 100 | 500 | 500 | 500 | 500 | 500 | 500 | 500 | 00 |
| (XVI) | pH 6.8 | <10 | 50 | 25 | 25 | 50 | 25 | 25 | 25 | 25 |
| | pH 8.2 | 250 | 500 | 250 | 100 | 250 | 50 | 250 | 250 | 50 |
| (XVII) | pH 6.8 | 9 | >500 | >500 | >500 | >500 | >500 | >500 | >500 | >500 |
| | pH 8.2 | 25 | >500 | >500 | >500 | >500 | >500 | >500 | >500 | >500 |
| (XVIII) | pH 6.8 | 500 | 500 | 500 | 500 | 500 | 500 | 500 | 500 | 500 |
| | pH 8.2 | 500 | >500 | 250 | >500 | >500 | >500 | >500 | >500 | >500 |
| (XIX) | pH 6.8 | 9 | 500 | 500 | 500 | 500 | 500 | 500 | 500 | 9 |
| | pH 8.2 | 9 | >500 | 500 | >500 | >500 | >500 | >500 | >500 | 9 |
| (XX) | pH 6.8 | 9 | 500 | 500 | 500 | 500 | 500 | 500 | 500 | 9 |
| | pH 8.2 | 9 | >500 | 250 | >500 | >500 | >500 | >500 | >500 | 9 |
| (XXI) | pH 6.8 | 9 | 500 | 500 | 500 | 500 | 250 | 250 | 500 | 500 |
| | pH 8.2 | 100 | >500 | 250 | >500 | >500 | >500 | >500 | >500 | >500 |
| (XXII) | pH 6.8 | 9 | 500 | 500 | 500 | 500 | 500 | 500 | 500 | 500 |
| | pH 8.2 | 25 | >500 | 500 | >500 | >500 | >500 | >500 | >500 | 500 |
| (XXIII) | pH 6.8 | 500 | >500 | >500 | >500 | >500 | >500 | >500 | >500 | >500 |
| | pH 8.2 | 250 | 500 | >500 | >500 | >500 | >500 | >500 | >500 | >500 |
| (XXIV) | pH 6.8 | 500 | 500 | 500 | 500 | 500 | 500 | 500 | 500 | 500 |
| | pH 8.2 | 500 | >500 | 250 | >500 | >500 | >500 | >500 | >500 | >500 |
| (XXV) | pH 6.8 | 500 | 500 | 500 | 500 | 500 | 500 | 500 | 500 | 500 |
| | pH 8.2 | 500 | >500 | 500 | >500 | >500 | >500 | >500 | >500 | 500 |
| (XXVI) | pH 6.8 | 9 | 500 | 500 | 500 | 500 | 500 | 500 | 500 | 25 |
| | pH 8.2 | 9 | >500 | 250 | >500 | >500 | >500 | >500 | >500 | 25 |
| (XXVII) | pH 6.8 | 25 | 500 | 500 | 500 | 500 | 250 | 500 | 500 | 250 |
| | pH 8.2 | 25 | 500 | 500 | 500 | 500 | 500 | 250 | 500 | 25 |
| (XXVIII) | pH 6.8 | 500 | 500 | 500 | 500 | 500 | 500 | 500 | 500 | 500 |
| | pH 8.2 | 500 | >500 | 500 | >500 | >500 | >500 | >500 | >500 | 500 |
| (XXIX) | pH 6.8 | 50 | 500 | 500 | 500 | 500 | 500 | 500 | 500 | 500 |
| | pH 8.2 | 500 | >500 | 500 | >500 | >500 | >500 | >500 | >500 | 500 |
| (XXX) | pH 6.8 | 500 | 500 | 500 | 500 | 500 | 500 | 500 | 500 | 500 |
| | pH 8.2 | 500 | >500 | 250 | >500 | >500 | >500 | >500 | >500 | >500 |
| (XXXI) | pH 6.8 | 50 | 500 | 500 | 500 | 500 | 500 | 500 | 500 | 100 |
| | pH 8.2 | 25 | >500 | 250 | >500 | >500 | >500 | >500 | >500 | 50 |

TABLE III

Minimum Inhibitory Concentrations for Test Compounds in Yeast/Fungi Species (in ppm) at pH 5.5

| COMPOUND | An | Ca | PC | SC | Tv | Ap | Fo |
|---|---|---|---|---|---|---|---|
| STANDARD I | >500 | >500 | >500 | 500 | >500 | >500 | >500 |
| (I) | 2.5 | 2.5 | 2.5 | <1 | 2.5 | <1 | 2.5 |
| (II) | <10 | <10 | <10 | <10 | <10 | <10 | <10 |
| (III) | 5 | 5 | 2.5 | 2.5 | 2.5 | 2.5 | 2.5 |
| (IV) | 25 | <10 | 10 | 2.5 | 10 | 5 | 5 |
| (V) | 5 | 25 | 2.5 | 5 | 25 | 2.5 | 10 |
| (VI) | 5 | 5 | 10 | 5 | <1 | 2.5 | 5 |
| (VII) | 10 | 50 | 25 | 5 | 5 | 5 | 5 |
| (VIII) | 100 | 25 | >500 | 9 | 9 | 9 | 50 |
| (IX) | <10 | 50 | <10 | <10 | <10 | <10 | <10 |

TABLE III-continued

Minimum Inhibitory Concentrations for Test
Compounds in Yeast/Fungi Species (in ppm) at pH 5.5

| | | | | | | | |
|---|---|---|---|---|---|---|---|
| (X) | 5 | 5 | 5 | 2.5 | 2.5 | 2.5 | 5 |
| (XI) | 500 | 500 | 500 | 250 | 250 | 50 | 100 |
| (XII) | 25 | 10 | 100 | 10 | 10 | 10 | 10 |
| (XIII) | <10 | <10 | <10 | <10 | <10 | <10 | <10 |
| (XIV) | <10 | 25 | <10 | <10 | <10 | <10 | <10 |
| (XV) | 100 | 100 | 100 | 50 | 100 | 50 | 50 |
| (XVI) | 2.5 | 5 | 2.5 | 2.5 | 10 | 2.5 | 5 |
| (XVII) | 25 | 500 | 9 | 9 | 500 | 9 | 250 |
| (XVIII) | 9 | 250 | 9 | 9 | 250 | 9 | 100 |
| (XIX) | 5 | 25 | 2.5 | 1 | >500 | 2.5 | 500 |
| (XX) | 9 | 250 | 9 | 9 | >500 | 9 | 25 |

| COMPOUND (EXAMPLE NO.) | ORGANISMS | | | | | | |
|---|---|---|---|---|---|---|---|
| | An | Ca | PC | SC | Tv | Ap | Fo |
| (XXI) | 9 | 9 | 9 | 9 | 25 | 9 | 9 |
| (XXII) | 50 | 250 | 25 | 9 | 250 | 9 | 50 |
| (XXIII) | 25 | 250 | 50 | 9 | 250 | 9 | 100 |
| (XXIV) | 500 | 500 | 500 | 500 | 500 | 500 | 500 |
| (XXV) | 250 | 500 | 9 | 500 | >500 | 250 | >500 |
| (XXVI) | 25 | >500 | 2.5 | 2.5 | >500 | 5 | >500 |
| (XXVII) | 9 | 50 | 9 | 9 | 100 | 9 | 25 |
| (XXVIII) | 100 | 500 | 100 | 250 | >500 | 50 | 250 |
| (XXIX) | 9 | 9 | 9 | 9 | 9 | >500 | 9 |
| (XXX) | 50 | 100 | 9 | 9 | 250 | 25 | 100 |
| (XXXI) | 25 | 25 | 9 | 9 | 50 | 9 | 25 |

Marine Antifouling Activity

The present invention is also directed to a method for inhibiting marine organisms. The term "marine organisms" is meant to include marine animals, such as barnacles, serpulid, bryozoa, oysters and hydroids, and marine plants, such as green algae and brown algae. The method for inhibiting marine organisms comprises contacting a surface exposed to a marine environment in which marine organisms grow with a marine antifouling effective amount of the compound of this invention.

As appreciated by those skilled in the art, not all of the compounds disclosed herein are active at the same concentrations or against the same marine organism species. That is, there may be some compound-to-compound variation in marine antifouling potency and spectrum of marine antifouling activity. Furthermore, a compound's marine antifouling activity may be dependent on the specific materials with which the compound is formulated to form a marine antifouling composition.

As used herein, the term "marine antifouling effective amount" refers to that amount of one or a mixture of two or more of the compounds of this invention needed to exhibit inhibition of selected marine organisms. Typically, this amount varies from providing about 1 weight percent to about 30 weight percent of the compound to a marine antifouling composition which is used to treat a surface exposed to a marine environment in which marine organisms live or grow. Such amounts vary depending upon the particular compound tested and marine organism to be treated. Also, the exact concentration of the compounds to be added in the preparation of industrial and consumer formulations may vary within a product type depending upon the components of the formulation.

A composition comprising a marine antifouling effective amount of the compound will also comprise an inert diluent which may be, for example, in the form of a paint. Particularly preferred are those paints having a vinyl resin binder such as, for example, a plasticized polyvinyl chloride or a polyvinyl chloride-polyvinyl acetate type. Preferably, the binders are formulated as latexes or emulsions. In a paint composition, the compound of the present invention is preferably used in an amount from about 1 to about 30 weight percent and, most preferably, from about 10 to about 25 weight percent. In addition to vinyl resin binder paints, epoxy and polyurethane binder paints containing the compound may also be useful. Coatings and films prepared from paints comprising the compound of the present invention typically remain substantially free from build-up of marine organisms for periods ranging from about 3 to about 12 months, depending upon the concentration of the compound and the thickness of the applied coating or film.

The term "a surface exposed to a marine environment" refers to a surface where a marine organism naturally or normally lives or grows. Typically, such a surface will be an area that is in continual or periodic contact with a marine environment such as an ocean or other body of water. Typical surfaces include, for example, a ship hull.

The marine antifouling activity of the compounds of the present invention is demonstrated by the following techniques.

Test panels are prepared from clear, rigid polyvinyl chloride film that is 0.381×10−3 m thick and has one textured surface. The test panels are 0.1524 m by 0.1524 m squares that have 0.00635 m holes punched at corners on 0.127 m centers. A 0.102 square template, with a 0.067 m diameter hole at the center, is attached to the center of the textured surface of the test panels.

A candidate marine antifoulant compound (1.0 g) is stirred into a resinous latex binder (9.0 g). A portion of the compound/binder mixture (1.5 g) is added to the center of the test panel and uniformly spread over the circular area inside the template.

Water is added dropwise as needed to properly spread the compound/binder mixture. The template prevents the compound/binder mixture from spreading beyond the uncovered area. The test panel is allowed to sit for between 10 to 30 minutes until the edge of the spread compound/binder mixture has dried. The template is then removed. The test panel is then allowed to dry for 8 to 12 hours at room temperature.

Two test panels are prepared for each candidate marine antifoulant compound. Two control test panels are also prepared by only treating with the resinous latex binder. One test panel of each candidate marine surfactant compound is attached over a white background to the topside of an exposure support apparatus. The second test panel is attached over a black background to the underside of the exposure support apparatus. The exposure support apparatus is placed horizontally 0.0254 m under a marine surface with the white background topside facing up. The exposure support apparatus is exposed to the marine environment for both 6 and 10 weeks during which time the control test panels become substantially covered with mature marine organism growth on both the topside and underside exposures.

After being removed from the exposure support apparatus, each test panel is inspected and rated for marine organism growth on both the treated and untreated areas of the test panel, The marine organisms present on the treated and untreated areas are noted. The presence of algae spores and bacterial slime are noted but not included in rating each test panel. The test panels are rated on a scale from 10 (representing completely free of marine organism growth) to 0 (representing completely covered with marine organism growth).

In Table IV, the marine antifouling rating values for some of the active compounds of the present invention are set forth, as well as the ratings for control panels (with no marine antifouling compound and referred to in Table IV as "Control").

In addition, test panels were prepared using tributyl tin oxide, a known marine antifouling compound. One set of such panels used the tributyl tin oxide in a commercially available ship-hull paint (referred to in Table IV as "STANDARD II") which was employed in the same manner as the resinous latex binder used on the other test panels. A second set of such panels used the tributyl tin oxide at a 10 percent concentration in the resinous latex binder (referred to in Table IV as "STANDARD III").

TABLE IV

Marine Antifouling Rating for Test Compounds

| Compound (Example No.) | Marine Antifouling Ratings | | | |
|---|---|---|---|---|
| | 6 Week Test | | 10 Week Test | |
| | Top Panel | Bottom Panel | Top Panel | Bottom Panel |
| I | 7 | 7 | 4 | 3 |
| XVI | 9 | 9 | 4 | 9 |
| Control | 10 | 7 | 5 | 4 |
| STANDARD II | 10 | 10 | 9 | 9 |
| STANDARD III | 10 | 10 | 4 | 10 |

What is claimed is:

1. A compound corresponding to the formula:

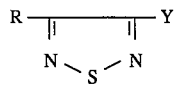

wherein R represents

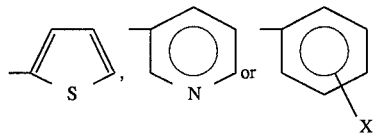

X represents H, —Br, —Cl, —F, —CH$_3$, —OCH$_3$, —COOCH$_3$, —NO$_2$, —SCH$_3$, —SO$_2$CH$_3$ or —CF$_3$ and Y is —SCN or —SCH$_2$SCN.

2. A compound as defined in claim 1 wherein Y represents —SCN.

3. A compound as defined in claim 1 wherein Y represents —SCH$_2$SCN.

4. The compound as defined in claim 3 which is 4-phenyl-3-thiocyanatomethylthio-1,2,5-thiadiazole.

5. An antimicrobial composition comprising an inert diluent and an antimicrobially-effective amount of a compound corresponding to the formula:

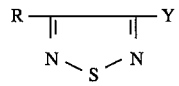

wherein R represents

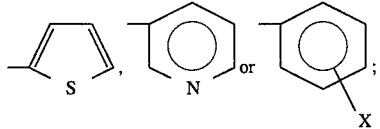

X represents H, —Br, —Cl, —F, —CH$_3$, —OCH$_3$, —COOCH$_3$, —NO$_2$, —SCH$_3$, —SO$_2$CH$_3$ or —CF$_3$ and Y is —SCN or —SCH$_2$SCN.

6. A composition of claim 5 wherein Y represents —SCN.

7. A composition of claim 5 wherein Y represents —SCH$_2$SCN.

8. The composition as defined in claim 7 wherein the compound is 4-phenyl-3-thiocyanatomethylthio-1,2,5-thiadiazole.

9. The composition of claim 5 wherein the compound is present in an amount to provide from about 1 part per million to about 5,000 parts per million by weight of the compound to a microbial habitat that is contacted with the composition.

10. A method for inhibiting microorganisms in a microbial habitat comprising contacting said microbial habitat with an antimicrobially-effective amount of a compound corresponding to the formula:

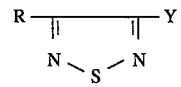

wherein R represents

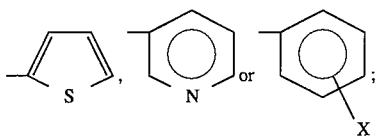

X represents H, —Br, —Cl, —F, —CH₃, —OCH₃, —COOCH₃, —NO₂, —SCH₃, —SO₂CH₃ or —CF₃ and Y is —SCN or —SCH2SCN.

11. A method of claim 10 wherein Y represents —SCN.

12. A method of claim 10 wherein Y represents —SCH₂SCN.

13. The method as defined in claim 12 wherein the compound is 4-phenyl-3-thiocyanatomethylthio-1,2,5-thiadiazole.

14. The method of claim 10 wherein the compound is present in the composition in an amount to provide from about 1 part per million to about 5,000 parts per million by weight of the compound to the microbial habitat.

15. A composition useful in preventing the growth of marine organisms on a surface exposed to a marine environment in which marine organisms grow comprising an inert diluent and a marine antifouling effective amount of a compound corresponding to the formula:

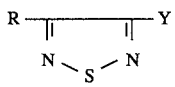

wherein R represents

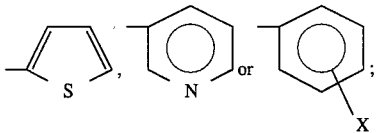

X represents H, —Br, —Cl, —F, —CH₃, —OCH₃, —COOCH₃, —NO₂, —SCH₃, —SO₂CH₃ or —CF₃ and Y is —SCN or —SCH₂SCN.

16. A composition of claim 15 wherein Y represents —SCN.

17. A composition of claim 15 wherein Y represents —SCH₂SCN.

18. The composition as defined in claim 17 wherein the compound is 4-phenyl-3-thiocyanato-methylthio- 1,2,5-thiadiazole.

19. The composition of claim 12 wherein the compound is present in the composition in an amount from about 1 weight percent to about 30 weight percent.

20. A method for preventing the growth of marine organisms on a surface exposed to a marine environment in which marine organisms grow comprising contacting said surface with a marine antifouling effective amount of a compound corresponding to the formula:

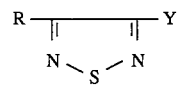

wherein R represents

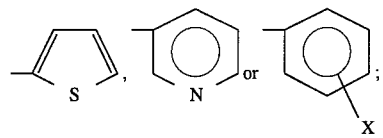

X represents H, —Br, —Cl, —F, —CH₃, —OCH₃, —COOCH₃, —NO₂, —SCH₃, —SO₂CH₃ or —CF₃ and Y is —SCN or —SCH₂SCN.

21. A method of claim 20 wherein Y represents —SCN.

22. A method of claim 20 wherein Y represents —SCH₂SCN.

23. The method as defined in claim 22 wherein the compound is 4-phenyl-3-thiocyanatomethylthio-1,2,5-thiadiazole.

24. The method of claim 20 wherein the compound is contacted with the surface in an amount from about 1 to about 30 weight percent of a composition comprising an inert diluent in admixture with the compound.

* * * * *